United States Patent [19]
Neward

[11] 3,946,736
[45] Mar. 30, 1976

[54] RESPIRATOR ASSIST DEVICE
[76] Inventor: Theodore C. Neward, 976 W. 9th St., Upland, Calif. 91786
[22] Filed: Oct. 18, 1974
[21] Appl. No.: 515,830

[52] U.S. Cl. .............................. 128/278; 128/356
[51] Int. Cl.² ................. A61M 1/00; A61B 17/24
[58] Field of Search ......... 128/.015, .016, 208, 245, 128/276, 278, 297, 351, 356

[56] References Cited
UNITED STATES PATENTS

| | | | |
|---|---|---|---|
| 2,756,742 | 7/1956 | Barton | 128/208 X |
| 3,050,062 | 8/1962 | Ulmer | 128/276 |
| 3,543,751 | 12/1970 | Sheffer | 128/208 |
| 3,730,179 | 5/1973 | Williams | 128/351 X |
| 3,809,079 | 5/1974 | Buttaravoli | 128/351 X |

*Primary Examiner*—Channing L. Pace
*Attorney, Agent, or Firm*—Lyon & Lyon

[57] ABSTRACT

A respirator assist device intended to be connected to a hand operated vacuum pump such as disclosed in U.S. Pat. No. 3,612,722 and includes a tubular tongue depressor and sealing means encircling the lips of the user; then, upon manually closing the nose of the user, and operating the pump, a vacuum is created in the throat above an object lodged therein, causing the object to be forced back into the mouth for removal.

4 Claims, 4 Drawing Figures

RESPIRATOR ASSIST DEVICE

BACKGROUND OF THE INVENTION

A common cause of death is due to lodging of an object, usually a large morsel of food in the region of the epiglottis or the entrance to the trachea in such a manner as to block passage of air to and from the lungs. For example, in the state of California, during the years 1970, 1971 and 1972, it is reported that the average number of deaths due to inhalation and injestion of food was 271, of which 256 persons were 9 years and over. If such blockage is complete, the victim will become unconscious in approximately two minutes; brain damage may occur after an additional three minutes and death will occur a few minutes later.

While a doctor or one trained to act in such emergencies may actually reach into the throat and remove the clogging object, or use an appropriate surgical instrument to relieve the condition, usually such help is not available within the extremely short time before permanent damage or death occurs. The problem is further complicated by the usual panic generated by such an event.

SUMMARY OF THE INVENTION

The present invention is directed to a respirator assist device which can overcome the problems indicated and is summarized in the following objects:

First, to provide a respirator assist device, which may be successfully manipulated by an unskilled person without injury to the victim and well within the short time span available.

Second, to provide a respirator assist device which is arranged to apply vacuum pressure to the mouth and the throat in such a manner that a pressure differential can be quickly established across the object which blocks the respiratory passage to cause the object to be dislodged and drawn to the back of the mouth and restore respiration.

Third, to provide a respirator assist device which utilizes a hand operated vacuum pump such as disclosed in U.S. Pat. No. 3,612,722, the pump requiring only a few strokes within a few seconds to produce the needed pressure differential, the pump also serving to determine whether or not the blockage is complete or only partial.

Fourth, to provide a respirator assist device, which is adapted to be inserted in the mouth to depress the tongue and insure a dependable passageway from the mouth, the device also being provided with a mouth encompassing seal means, the nose being closed separately either manually or by a clamp so that once the assist device has performed its service, nasal air flow can be quickly re-established.

Fifth, to provide a respirator assist device which may be manufactured at such low cost that it may be discarded after use.

Figure 1:
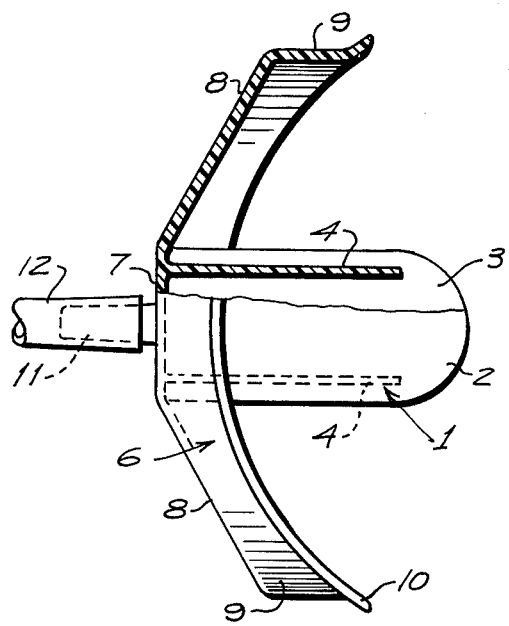
FIG. 1 is a top view of the respirator assist device with a portion shown in section.
Figure 2:
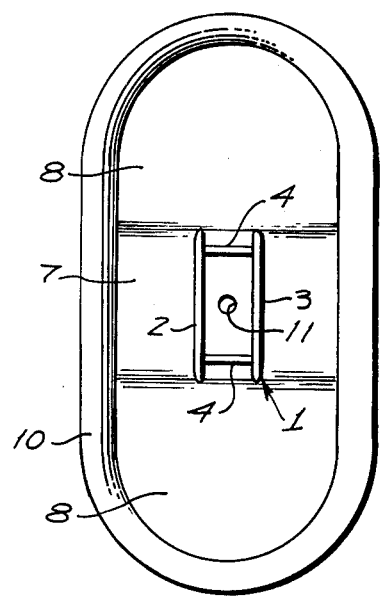
FIG. 2 is an end view thereof.

The respirator assist device includes a tubular member 1 which is rectangular in cross section and which includes a pair of plates 2 and 3 connected by side walls 4 spaced inwardly from the side margins of the plates. Each plate includes a rearwardly extending semi-circular portion 5.

The forward end of the tubular member 1 is joined integrally to a seal member 6 which includes a front wall 7, having a lateral angular portion 8. The front wall and the angular portions are provided with a peripheral wall 9 having an outwardly directed flange 10. The center of the front wall 7 is provided with a nipple 11 centered with respect to the tubular member 1.

The nipple is connected by an air tube 12 to a source of vacuum pressure. Preferably, the vacuum source is a hand vacuum pump designated 13 which is more fully described in U.S. Pat. No. 3,612,722. More specifically, the vacuum pump includes a fixed handle 14 connected to a cylinder 15 and a pivotable handle 16 connected to a piston rod 17. The handles are positioned so that they may be squeezed together, return movement being accomplished by a spring not shown. The cylinder 15 is joined to a stem 18 which is connected to the air tube 12. Between the stem 18 and cylinder 15 there is provided a suitable gauge 19.

The respirator assist device is used as described below: The usual cause of blockage of the flow of air to and from the lungs occurs upon the premature swallowing of a partially chewed morsel of food which becomes lodged in the region of the epiglottis, larynx or trachea.

Figure 3:
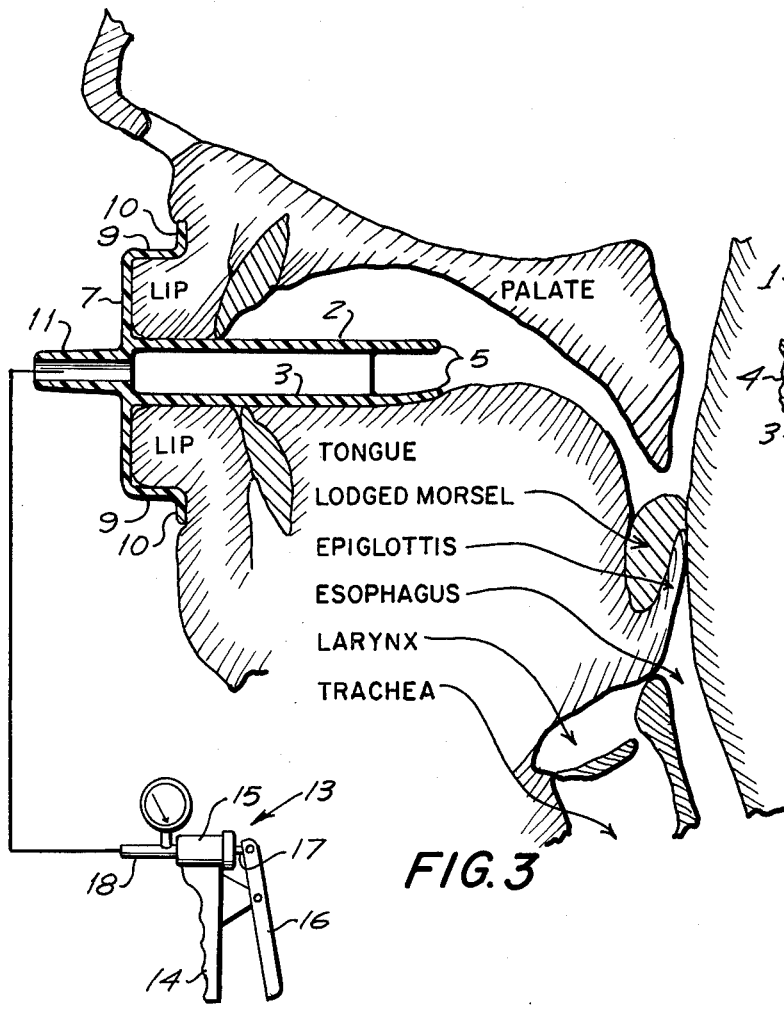
FIG. 3 is a longitudinal sectional view thereof shown in position within a person's mouth adjacent portions of the mouth and throat being indicated in section and showing a typical location of a lodged food particle.
Figure 4:
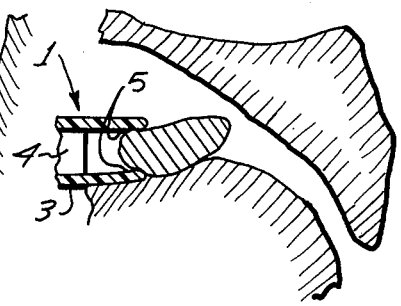
FIG. 4 is a fragmentary view similar to FIG. 3, showing the food particle as it may appear when dislodged and moved to the back of the mouth.

The tubular member 1 is inserted into the mouth of the victim as soon as possible, and is forced inward until the seal member 6 encompasses the lips of the victim as indicated in FIG. 3, causing the lower plate to depress the tongue so that an air passage is maintained which communicates with the throat at the back side of the tongue.

Preferably the tubular member 1 is preconnected to the air tube 12 and to the vacuum pump 13 so that when the member 1 and seal member 6 are in place, the vacuum pump may be immediately operated. During pumping time, the nose of the victim is held closed either manually or by a suitable clamp.

A few strokes of the hand pump usually produce sufficient vacuum pressure within the upper portion of the throat such that a pressure differential is created across the food morsel of sufficient magnitude that the ambient pressure within the lungs is sufficient to drive the morsel upwardly into the mouth against the inner end of the tubular member 1, or the size of the morsel may be such as to be drawn into the tubular member as wedge therein. In either case, the vacuum pressure is released by releasing the victim's nose. Should the vacuum pressure in the nose prevent the nose from opening, the vacuum pump is provided with a release valve, not shown, or the air tube may be disconnected. When atmospheric pressure is restored in the mouth, the tubular member 1 and the morsel are removed.

If the victim is merely choking on the food morsel, but is still able to breathe, use of the device will do no harm, and observation of the gauge will show no appreciable reduction in pressure.

The amount of pumping required to produce a substantial vacuum pressure such as a drop up to approximately twenty inches of mercury occurs rather rapidly if the food morsel is completely blocking the lungs; whereas, if the lungs are not completely blocked, the same amount of pumping will produce only nominal vacuum pressure. Thus, its readily determinable whether or not, there is in fact, a complete blockage. In the case of complete blockage, only a few seconds of time need elapse before the morsel can be forced free, well within the two minutes of time before damage is done.

It will be observed that the portions of the tubular member 1 and seal member 6 above and below a medium plane therethrough are identical. As a consequence, the tubular member 1 may be inserted either side up so that either plate may become the lower plate and serve to depress the tongue. The upper plate serves to maintain the lower or tongue depressing plate in spaced relation to the palate so as to insure that the tongue does not cause a blockage at the rear of the mouth.

It is, of course, necessary that the respiratory assist device be of approximately the right size; however, a large number of sizes is not required. A large size will accommodate most men; a ten percent smaller size will accommodate most women and older children, approximately two-thirds the large size and small size will accommodate small children. In this regard it should be noted that the variation in head size of an individual is not as great as the variation in other body measurements.

While reference has been made to the food morsel as the source of blockage, the blocking object may be other than food, particularly among children. For example, marbles or other objects may be lodged in the throat.

The respirator assist device is preferably injection molded as a single piece from a plastic material which is capable of sterilization and is sufficiently low in cost that the device may be discarded after use. By way of example, but not limitation, a suitable material is a high impact styrene.

Tests have indicated that the large size of the respirator assist device may have plates, approximately 2¾ inches long and 1 inch wide, and their external surfaces may be spaced about ½ inch. These dimensions enable the rear portion of an adult male's tongue to be adequately spaced from the palate to insure communication to the throat.

Having fully described my invention it is to be understood that I am not to be limited to the details herein set forth, but that my invention is of the full scope of the appended claims.

I claim:

1. A respirator assist device for removal of an object lodged in the throat, said device comprising:
   a. a mouth covering plate having a marginal flange dimensioned to encase and seal the lips of the user;
   b. a pair of flat blade elements extending from the mouth covering plate;
   c. a pair of wall elements extending from the covering plate and joined to the balde elements to form a passageway;
   d. the blade elements being insertable between the palate and the tongue of the user to depress the tongue from the palate, the covering plate limiting the depth of insertion of the blade elements to prevent contact with the back of the mouth and throat;
   e. and means communicating with the passageway through the mouth covering plate for producing a negative pressure in the passageway thereby to produce a pressure differential across an object lodged in the throat and urge the object toward the blade elements.

2. A respirator device as defined in claim 1, wherein:
   a. the mouth covering plate is symmetrical along the plane of the passageway midway between the blade elements whereby either blade element may engage and depress the tongue, and the mouth covering plate in either position of the blade elements is sealingly engageable with the lips.

3. A respirator device as defined in claim 1, wherein:
   a. the mouth covering plate, blade elements and wall elements are integral.

4. A respirator assist device for removal of an object lodged in the throat, said device comprising:
   a. a mouth covering plate approximating the curvature of the face of the user for surrounding the mouth and including a marginal flange having a portion fitting between the lips and the nose of the user, the marginal flange being pressible against the lips of the user to form a seal;
   b. an integral tubular extension centered between the marginal flange for insertion into the mouth of the user, the tubular extension including a pair of spaced essentially flat, blade elements either blade element being engageable with the tongue when the mouth covering plate is in sealing engagement with the user's face;
   c. and means carried by the mouth covering plate for connection to a sourse of negative pressure thereby to produce a pressure differential across an object lodged in the user's throat urging the object toward the tubular extension.

* * * * *